(12) United States Patent
Wang

(10) Patent No.: US 12,016,530 B2
(45) Date of Patent: Jun. 25, 2024

(54) THERAPEUTIC ENDOSCOPE

(71) Applicant: TECHEVERST CO., LTD., Taipei (TW)

(72) Inventor: Pa-Chun Wang, Taipei (TW)

(73) Assignee: TECHEVERST CO., LTD., Taipei (TW)

( * ) Notice: Subject to any disclaimer, the term of this patent is extended or adjusted under 35 U.S.C. 154(b) by 506 days.

(21) Appl. No.: 16/938,361

(22) Filed: Jul. 24, 2020

(65) Prior Publication Data

US 2021/0321862 A1 Oct. 21, 2021

(30) Foreign Application Priority Data

Apr. 15, 2020 (TW) .................................. 109112711

(51) Int. Cl.
*A61B 1/018* (2006.01)
*A61B 1/00* (2006.01)
*A61B 1/04* (2006.01)
*A61B 1/227* (2006.01)

(52) U.S. Cl.
CPC .......... *A61B 1/018* (2013.01); *A61B 1/00052* (2013.01); *A61B 1/04* (2013.01); *A61B 1/227* (2013.01)

(58) Field of Classification Search
None
See application file for complete search history.

(56) References Cited

U.S. PATENT DOCUMENTS

| 799,114 | A | * | 9/1905 | Tracey | A61B 1/00101 600/127 |
| 4,622,954 | A | * | 11/1986 | Arakawa | A61B 1/0051 600/153 |
| 5,759,150 | A | * | 6/1998 | Konou | A61B 18/1485 606/190 |
| 5,938,590 | A | * | 8/1999 | Elliott | A61B 1/00087 606/162 |
| 6,106,457 | A | * | 8/2000 | Perkins | A61B 1/00105 600/172 |

(Continued)

FOREIGN PATENT DOCUMENTS

| CN | 202397438 U | 8/2012 |
| TW | M520876 U | 5/2016 |
| WO | WO-2013/022212 A2 | 2/2013 |

OTHER PUBLICATIONS

Machine English Translation CN202397438U Dec. 18, 2011 Sun, Cai-bo; Li, Ling-fang.*

(Continued)

*Primary Examiner* — John P Leubecker
(74) *Attorney, Agent, or Firm* — Muncy, Geissler, Olds & Lowe, P.C.

(57) ABSTRACT

The present disclosure relates to a therapeutic endoscope. The therapeutic endoscope includes a main body, an image sensor unit connected to the main body, and a cover attached to the main body. The cover includes a first opening adjacent to the image sensor unit, a second opening opposite to the first opening, and a sidewall extending between the first opening and the second opening. The sidewall of the cover includes a third opening connecting the first opening and the second opening. The present disclosure also relates to a cover for a therapeutic endoscope.

11 Claims, 5 Drawing Sheets

(56) References Cited

U.S. PATENT DOCUMENTS

| | | | | |
|---|---|---|---|---|
| 6,165,125 A * | 12/2000 | Elliott | A61B 1/00087 | 600/184 |
| 6,306,084 B1 * | 10/2001 | Pinczower | A61B 10/0233 | 600/184 |
| 6,390,975 B1 * | 5/2002 | Walls | A61B 1/32 | 600/200 |
| 7,588,580 B2 * | 9/2009 | Okada | A61B 18/14 | 606/113 |
| 7,691,120 B2 * | 4/2010 | Shluzas | A61B 17/7083 | 606/198 |
| 8,131,380 B2 * | 3/2012 | Cao | A61B 1/31 | 606/41 |
| 8,167,893 B2 * | 5/2012 | Motosugi | A61B 18/14 | 606/113 |
| 8,721,527 B2 * | 5/2014 | Braam | A61B 17/320036 | 600/114 |
| 10,278,572 B1 * | 5/2019 | Clark | A61B 17/02 | |
| 10,702,305 B2 * | 7/2020 | Garofalo | A61B 17/3423 | |
| 10,779,824 B2 * | 9/2020 | Shelton, IV | A61B 17/29 | |
| 2007/0261494 A1 * | 11/2007 | Fuller | A61B 8/445 | 73/620 |
| 2008/0177135 A1 * | 7/2008 | Muyari | A61B 1/00087 | 600/104 |
| 2008/0208006 A1 * | 8/2008 | Farr | A61B 1/0676 | 600/178 |
| 2012/0088976 A1 * | 4/2012 | Shehadeh | A61B 1/00101 | 600/187 |
| 2012/0289858 A1 * | 11/2012 | Ouyang | A61B 1/00039 | 600/562 |
| 2015/0133732 A1 * | 5/2015 | Goldfain | A61B 1/227 | 600/200 |
| 2018/0084999 A1 * | 3/2018 | Oved | A61B 3/0025 | |
| 2019/0117258 A1 * | 4/2019 | Yamauchi | A61F 11/00 | |
| 2020/0178776 A1 * | 6/2020 | Kwong | A61B 1/042 | |
| 2020/0345212 A1 * | 11/2020 | Dreyer | A61B 1/00112 | |
| 2022/0167841 A1 * | 6/2022 | Keogh | A61G 13/121 | |

OTHER PUBLICATIONS

Office Action dated Oct. 8, 2020 in TW Application No. 109112711, 9 pages.

* cited by examiner

FRIOR ART

THERAPEUTIC ENDOSCOPE

BACKGROUND OF THE INVENTION

1. Field of the Invention

The present invention relates to a therapeutic endoscope, and in particular to a cover for a therapeutic endoscope.

2. Description of the Related Art

Endoscope is a medical device that can be used to observe the internal condition in human. A user (such as medical personnel) can guide the endoscope or a part of the endoscope to enter the body of a patient to examine and treat the patient. How to improve efficiency over which the user uses the endoscope to examine/treat the subject and increase the accuracy of the examination/treatment are problems to be solved urgently in the technical field of the disclosure.

SUMMARY OF THE INVENTION

The present disclosure relates to a therapeutic endoscope. The therapeutic endoscope includes a main body, an image sensor unit connected to the main body, and a cover attached to the main body. The cover includes a first opening adjacent to the image sensor unit, a second opening opposite to the first opening, and a sidewall extending between the first opening and the second opening. The sidewall of the cover includes a third opening connecting the first opening and the second opening.

The present disclosure also relates to a cover for a therapeutic endoscope. The cover includes a first opening, a second opening opposite to the first opening, and a sidewall extending between the first opening and the second opening. The sidewall includes a third opening connecting with the first opening and the second opening.

BRIEF DESCRIPTION OF THE DRAWINGS

Various aspects of at least one embodiment are discussed below with reference to the accompanying drawings, and the drawings are not intended to be drawn to scale. Where technical features accompany component symbols in the drawings, embodiments, or claims, such component symbols are included for the sole purpose of increasing intelligibility in the drawings, embodiments, or claims. Therefore, whether the component symbols exist is not intended to have a limiting effect on the scope of the claims. In the drawings, the same or nearly the same components shown in the various drawings are represented by the same number. For clarity, not every component is labeled in every drawing. Such drawings provide a definition that is not considered as a limitation on the present invention for the purpose of illustration and explanation. In the drawings:

PREFERRED EMBODIMENT OF THE PRESENT INVENTION

Figure 1:
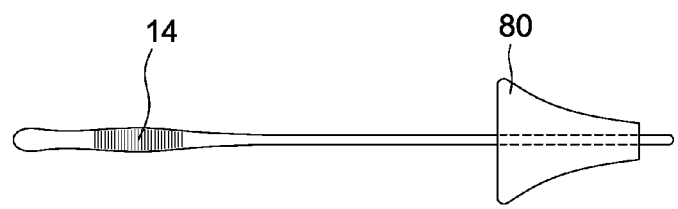
FIG. 1 is a side view of a cover and a medical device.

FIG. 1 is a side view of a cover 80 (or catheter) and a medical device 14. The cover 80 can be attached to a main body of an endoscope directly or via a connector. For example, the cover 80 can be connected to an otoscope, rhinoscope, hysteroscope, colposcope, cystoscope, gastroscope, anoscope, or other endoscope for observing and/or treating human structure.

As shown in FIG. 1, the cover 80 has a funnel shape. During use, the cover 80 can be extended into an external aperture of the body of a patient to allow a user (such as a medical personnel) to observe the internal structure of the patient. For example, when the cover 80 is used in combination with an otoscope, an end of the cover 80 with a larger diameter is attached to the otoscope, and an end of the cover 80 with a smaller diameter is placed in the ear canal of the patient. The cover 80 has a light-gathering function, and the user can observe the internal condition in the ear canal of the patient through the otoscope. However, when the user intends to extend the medical device 14 into the ear canal of the patient through the cover 80 for treatment, the sight of the user is blocked, and also the field of view of the user and the operating space of the device are restricted, since the work axis of the medical machine 14 is overlapped with the user's visual axis. Therefore, it is difficult (or even impossible) for the user to observe and treat the patient at the same time. This will prevent the treatment of the patient and affect the treating accuracy.

According to some embodiments of the present disclosure, an otoscope with an digital display can be used, rather than directly observing the patient through the otoscope and the cover 80 by the user. In particular, the user can put an image sensor unit into the ear canal of the patient. The image sensor unit is connected (via wired or wireless connection) to a display device to transfer an image of the ear canal of the patient to the display device for observation by the user. However, when the user intends to extend the medical device 14 into the ear canal of the patient through the cover 80 for treatment, the user has to remove the image sensor unit from the ear canal of the patient before treatment with the medical machine 14, since the working axis of the medical machine 14 is overlapped with the user's visual axis. Therefore, the problem of simultaneous observation and treatment cannot be solved.

Figure 2:
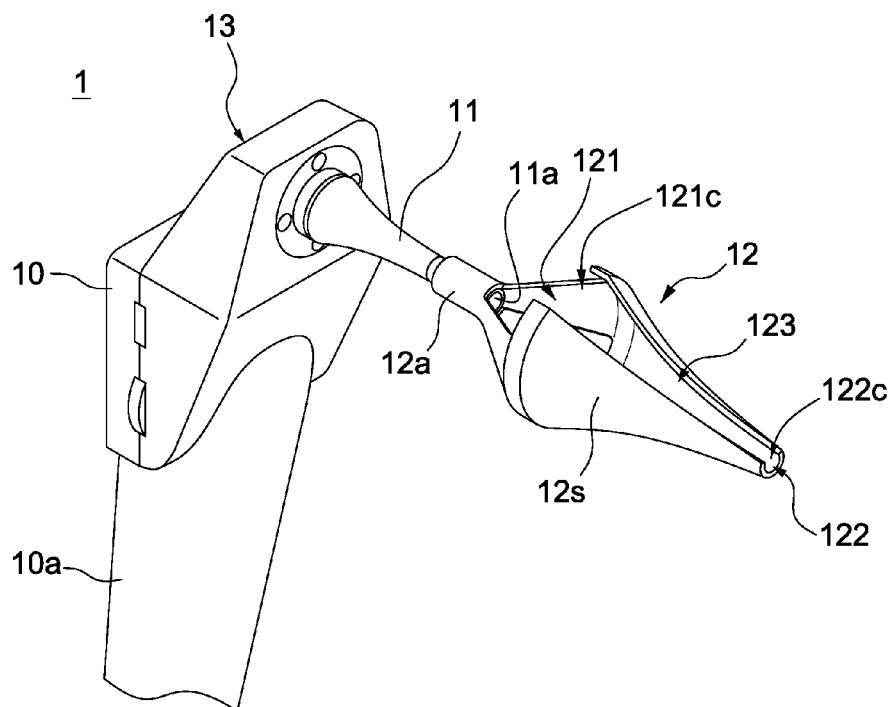
FIG. 2 is a three-dimensional view of a therapeutic endoscope according to some embodiments of the present invention.
Figure 3:
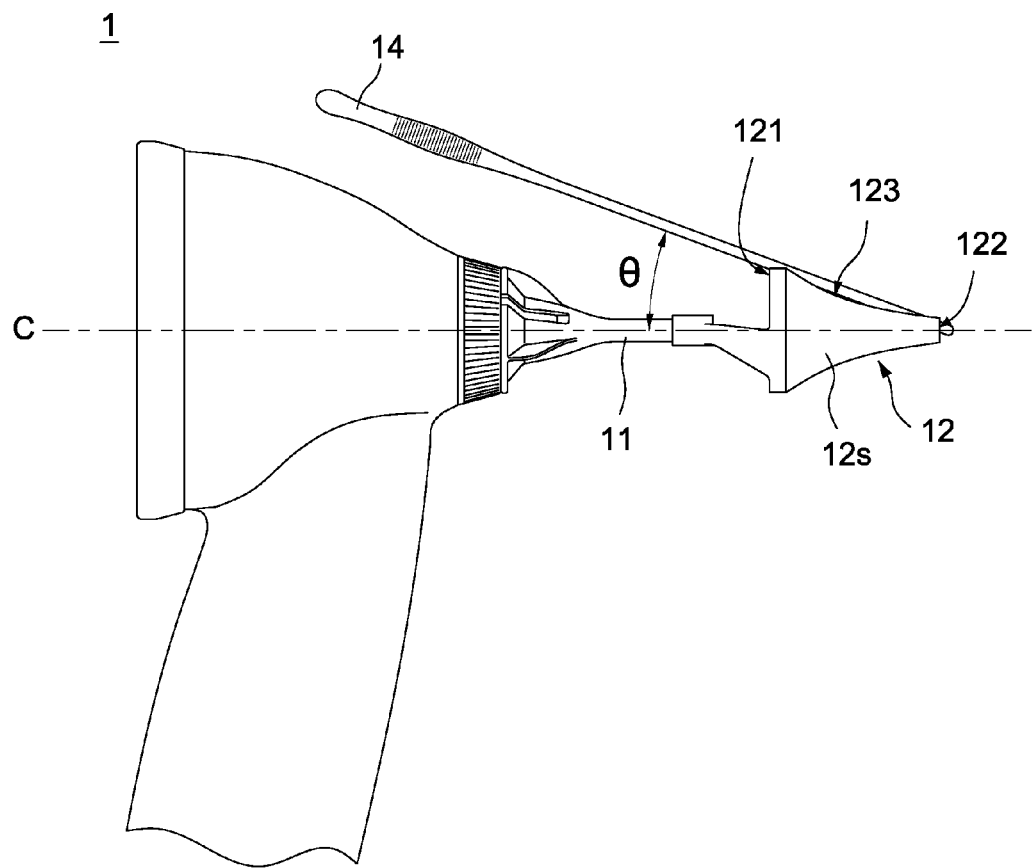
FIG. 3 is a side view of a therapeutic endoscope and a medical device according to some embodiments of the present invention.

FIG. 2 is a three-dimensional view of a therapeutic endoscope 1 according to some embodiments of the present invention. FIG. 3 is a side view of a therapeutic endoscope 1 and a medical device 14 according to some embodiments of the present invention. The therapeutic endoscope 1 includes a main body 10, an image sensor unit 11, a cover 12 (or catheter), and a display 13. According to some embodiments of the present disclosure, the endoscope 1 can be an otoscope, a rhinoscope, a hysteroscope, a colposcope, a cystoscope, a gastroscope, or other endoscopes for observing and/or treating human organs.

The main body 10 can include a handle 10a, and a user may use the therapeutic endoscope 1 by holding the handle 10a.

The image sensor unit 11 is connected to main body 10. According to some embodiments of the present disclosure, the main body can include a protruding portion for accommodating the image sensor unit 11. In some embodiments, the image sensor unit 11 may include (without limitation) a plurality of optical elements (such as lenses), light sensing areas (such as pixels), and lens 11a. As shown in FIG. 2, the lens 11a is provided at a front end of the protruding portion of the main body 10. The image sensor unit 11 can be configured to capture pictures or images. According to some embodiments of the present disclosure, the lens 11a of the image sensor unit may be located on or near the central axis of the cover 12 (the axis C shown in FIG. 3). According to various design aspects, the lens 11a of the image sensor unit may be located anywhere in the cover 12.

The display 13 is connected to the image sensor unit 11 (via wired or wireless connection) and is configured to display the pictures or images captured by the image sensor unit 11. According to some embodiments of the present disclosure, the display 13 is attached to the main body 10, and the direction of the display 13 is opposite to the lens 11a so that the display faces the user when used by the user. According to some embodiments of the present disclosure, the display 13 can also be separated from the main body. For example, the display 13 can be an independent display.

The cover 12 is connected to the main body 10 or the image sensor unit 11. According to some embodiments of the present disclosure, the cover 12 has a connecting member 12a, which can be connected to the front end of the protruding portion of the image sensor unit 11. The connecting member 12a has an opening to expose the lens 11a of the image sensor unit 11. According to other embodiments of the present disclosure, the cover 12 may be integrally formed with the main body 10 or the image sensor unit 11.

In some embodiments, the cover 12 may include a material with elasticity, such as silicone, rubber, or other materials that can be elastically deformed to a certain degree. In some embodiments, the cover 12 may include a material that is not elastic (for example, the amount of elastic deformation is small or almost zero). For example, the cover 12 may include a material with rigidity, so that the user can place the cover 12 into an aperture with strong muscle contractility (e.g., anus, vagina, and cervix, etc.) in the human body. According to some embodiments of the present disclosure, when the cover 12 is squeezed or pulled, the amount of deformation of the opening 123 is less than or equal to 10%.

The cover 12 has an opening 121 and an opening 122 opposite to the opening 121. According to some embodiments of the present disclosure, the diameter (or tube diameter) of the opening 121 is larger than the diameter of the opening 122. For example, the cover 12 may have a funnel shape. For example, in a direction facing the lens 11a, the projection area of the opening 121 may be larger than the projection area of the opening 122. For example, in the direction from the lens 11a toward the opening 122, the projected area of a side wall 12s gradually decreases. According to other embodiments of the present disclosure, the diameter of the opening 121 may also be equal to the diameter of the opening 122. For example, the cover 12 may be cylindrical. For example, in the direction facing the lens 11a, the projection area of the opening 121 may be equal to the projection area of the opening 122.

The cover 12 has the side wall 12s that extends or connects between the opening 121 and the opening 122. The side wall 12s has an opening 123. The opening 123 connects the opening 121 and the opening 122. For example, the opening 123 extends between the opening 121 and the opening 122. A notch 121c is formed at the junction between the opening 121 and the side wall 12s. For example, the boundary of the opening 121 defines the notch 121c. In some embodiments, the center angle of the notch 121c is greater than 0° and less than 180°. Similarly, a notch 122c is formed at the junction between the opening 122 and the side wall 12s. For example, the boundary of the opening 122 defines the notch 122c. In some embodiments, the center angle of the notch 122c is greater than 0° and less than 180°. According to some embodiments of the present disclosure, the center angle of the notch 122c is smaller than the center angle of the notch 121c. According to other embodiments of the present disclosure, the center angle of the notch 122c may be equal to or greater than the center angle of the notch 121c. According to some embodiments of the present disclosure, the gap of the notch 121c is larger than the gap of the notch 122c. According to other embodiments of the present disclosure, the gap of the notch 121c may be equal to or smaller than the gap of the notch 122c. According to some embodiments of the present disclosure, the cover 12 can rotate clockwise and counterclockwise relative to the image sensor unit 11, so the opening 123 can be oriented upward, right, left, downward, or toward any other direction according to actual needs.

In use, the user positions the cover 12 of the therapeutic endoscope 1 into an aperture close to the site to be examined (for example, ear canal, nostril, mouth, urethra, vagina, and anus.) in a patient. The lens 11a of the image sensor unit 11 is configured to capture the picture or image of the site to be examined of the patient through the opening 121 and the opening 122, and send it to the display 13 for observation and diagnosis by the user.

As shown in FIGS. 2 and 3, when the user intends to use the medical device 14 for treatment, the medical device 14 can be inserted through the opening 123 and extended into the aperture of the patient through the opening 122 for treatment. The medical device can move freely in the opening 123 without blocking the user's sight. In addition, the user can view the pictures or images of internal organs of the patient from the display 13 upon treatment with a medical device without removing the therapeutic endoscope 1 from the human body, thereby achieving the effect of simultaneous diagnosis and treatment.

As shown in FIG. 3, the image sensor unit 11 of the therapeutic endoscope 1 has a central axis (or optical axis) C. The central axis C extends through the opening 121 and the opening 122. When the medical device 14 is used with the therapeutic endoscope 1, the medical device 14 defines an angle θ with respect to the central axis C. In some embodiments, the angle θ may be between about 15° and about 90°, for example, the angle θ may be about 80°, about 70°, about 60°, about 50°, about 40°, about 30° or other values.

Figure 4:
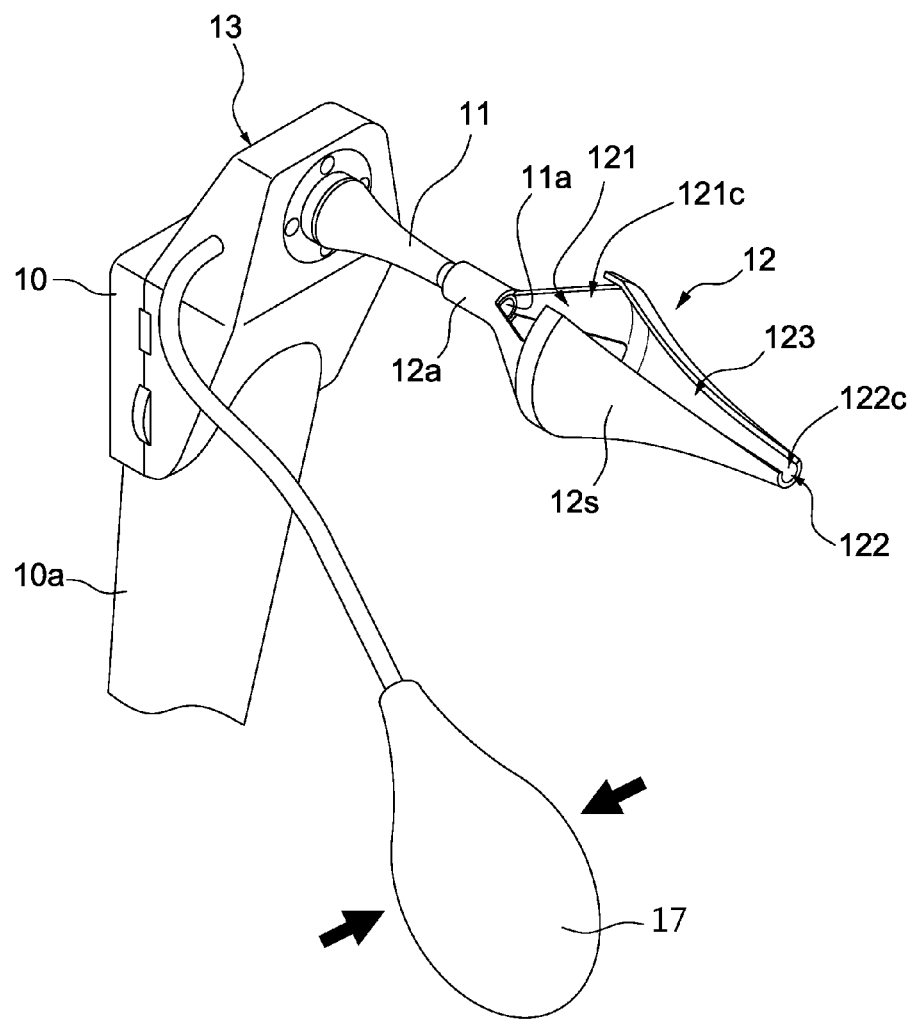
FIG. 4 is a three-dimensional view of a therapeutic endoscope according to some embodiments of the present invention.

FIG. 4 is a three-dimensional view of a therapeutic endoscope 4 according to some embodiments of the present invention. The therapeutic endoscope 4 shown in FIG. 4 includes the therapeutic endoscope 1 shown in FIG. 2 and a jet ball 17.

The jet ball has a jet port, a ball, and a connecting tube. The jet port can be disposed at the inside of the side wall of the cover 12, and connected to the ball by the connecting tube, so when a user presses the ball, the airflow can be vented from the jet port via the connecting tube. The user can use the jet ball to observe the effect of airflow in the body (for example, on the eardrum) of the patient. In some embodiments, the airflow from the air-jet ball can be used by the user to push open the aperture (e.g. anus, vagina, cervix, etc.) with strong muscle contractility in the human body.

Figure 5A:
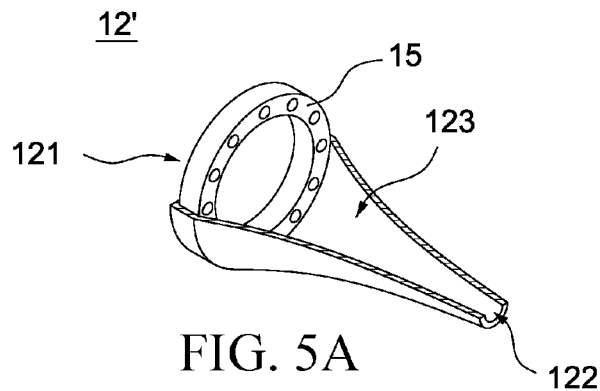
FIG. 5A is a three-dimensional view of a cover for a therapeutic endoscope according to some embodiments of the present invention.
Figure 5B:
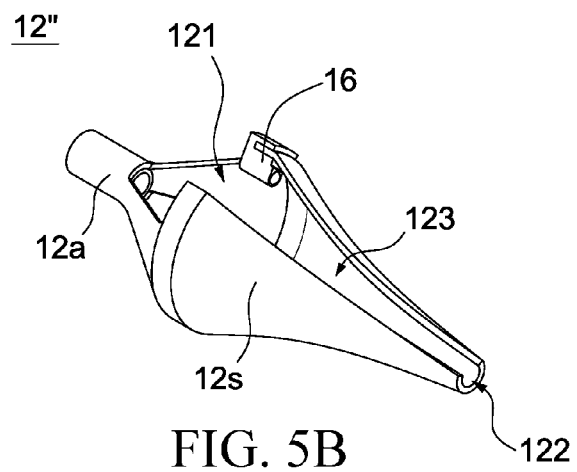
FIG. 5B is a three-dimensional view of a cover for a therapeutic endoscope according to some embodiments of the present invention.
Figure 5C:
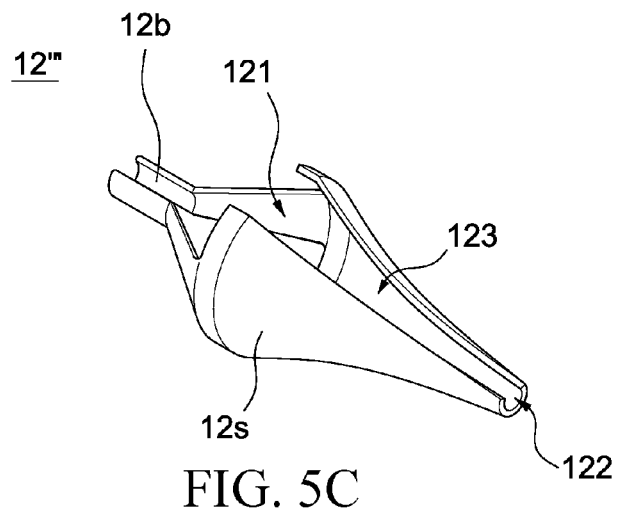
FIG. 5C is a three-dimensional view of a cover for a therapeutic endoscope according to some embodiments of the present invention.

FIGS. 5A, 5B, and 5C are three-dimensional views of covers 12', 12", and 12'" for a therapeutic endoscope according to some embodiments of the present invention. The cover 12 shown in FIGS. 2, 3 and 4 can be replaced with the cover 12', 12", and 12" shown in FIGS. 5A, 5B and 5C.

Referring to FIG. 5A, the cover 12' has a ring-shaped light emitting element 15 disposed at the opening 121. The ring-shaped light emitting element 15 is configured to emit a light source toward the opening 122. In some embodiments, when used with a medical device, the medical device may temporarily block the light source. Since the ring-shaped light-emitting element 15 can supplement the light source at various angles, the use of the ring-shaped light-emitting element 15 as shown in FIG. 5A can provide sufficient light source to the user at any time.

Referring to FIG. 5B, the cover 12" has a light emitting element 16 disposed at the opening 121. The light-emitting element 16 can be disposed at any position to supplement the light source. Compared with the ring-shaped light-emitting element 15 shown in FIG. 5A, the light-emitting element 16 shown in FIG. 5B has higher design flexibility and lower cost. For example, in some embodiments, the light emitting element 16 may be disposed at the junction of the opening 121 and the opening 123. In some embodiments, the light emitting element 16 may be disposed on the side wall defining the opening 123. In some embodiments, the distance between the light emitting element 16 and the opening 122 can be adjusted as desired In some embodiments, the light source of the light emitting element 16 may be disposed on the inner surface of the cover 12". In some embodiments, the light source of the light emitting element 16 may be disposed on the outer surface of the cover 12".

In some embodiments, the cover 12 (or other covers 12', 12", and 12'" shown in FIGS. 5A to 5C) may have an inner surface that can reflect light, so as to reflect and enhance the light from the light emitting element (such as light emitting elements 15, and 16). For example, the inner surface of the cover 12 may have a liner that reflects light. In some embodiments, the light-reflecting liner may have any pattern (for example, stripes, grids, and other patterns), and may be arranged at any position. For example, in some embodiments, the light-reflecting liner may be provided in conjunction with a light emitting element (e.g., light emitting elements 15 and 16). For example, in some embodiments, the light-reflecting liner may be arranged at a position where it is easier to reflect the light of the light-emitting element.

Referring to FIG. 5C, the cover 12'" shown in FIG. 5C can be clamped around the lens 11a by means of a clamp 12b. In some embodiments, the cover discussed herein may be optionally otherwise attached to the main body (for example, main body 10 shown in FIG. 2), and the present invention is not limited to the aspect illustrated in the drawings.

Figure 6:
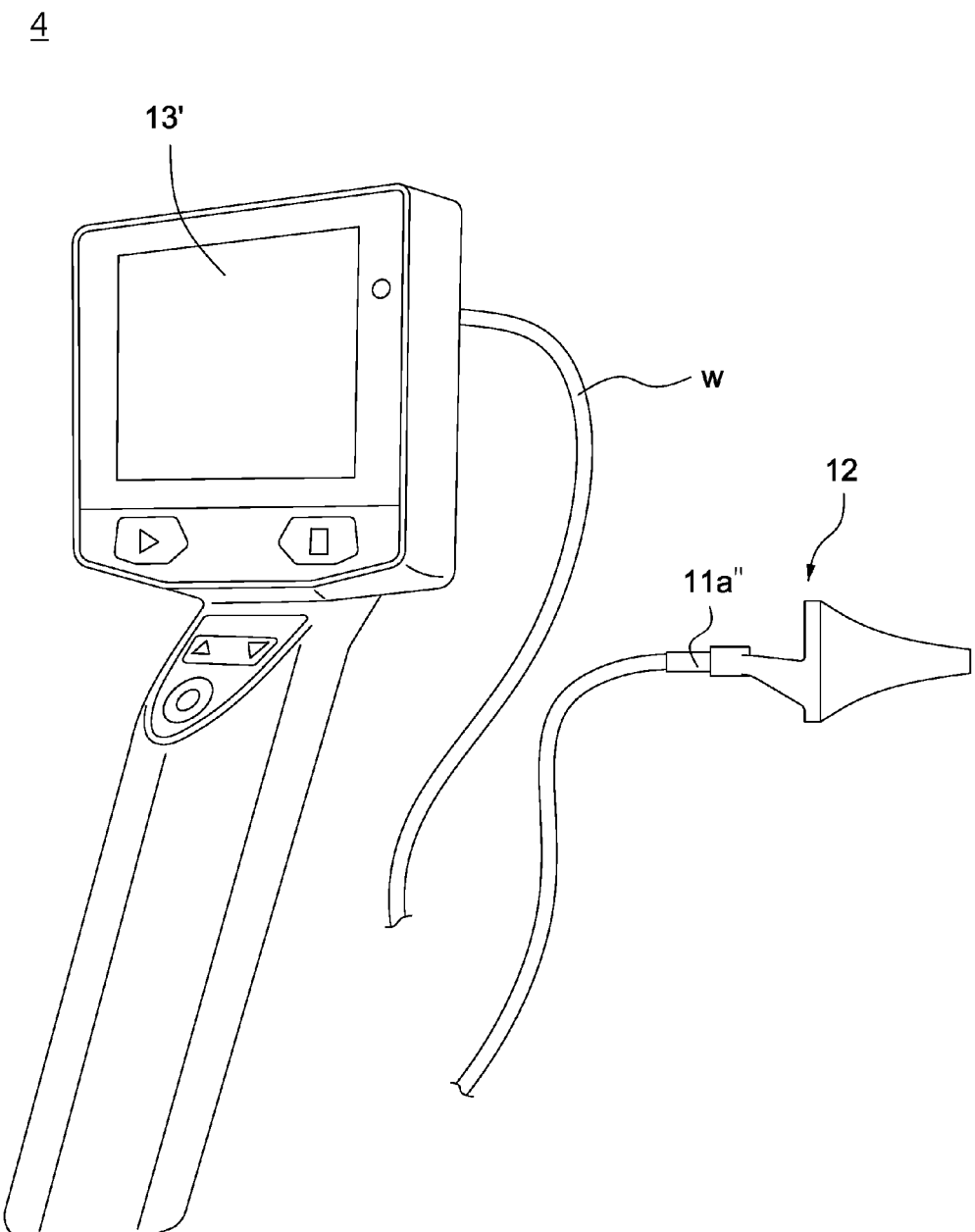
FIG. 6 is a three-dimensional view of a therapeutic endoscope according to some embodiments of the present invention.

FIG. 6 is a three-dimensional view of a therapeutic endoscope 6 according to some embodiments of the present invention. The cover 12 (or other covers 12', 12", and 12'" shown in FIGS. 5A to 5C) can be connected to the lens 11a" (or other lens 11a shown in FIG. 2). The lens 11a" is connected to an external display 13' via electrical connector w (such as a wire). The display 13' can present the image sensed by the lens 11a", and the user can view the state in the patient from the display 13'. The user can hold the electrical connector w to manipulate the lens 11a".

It is to be understood that, the embodiments of the method and apparatus discussed herein are not limited to details of the construction and configuration of the components provided in the following description or depicted in the accompanying drawings in application. The method and apparatus may be implemented in other embodiments and may be practiced or executed in various ways. Examples of specific implementations are provided herein for the purpose of illustration only and are not intended to be limiting. In particular, actions, components, and features discussed with reference to any one or more embodiments are not intended to be excluded from a similar role in any other embodiment.

Moreover, the phraseology and terminology used herein are for the purpose of description and should not be regarded as limiting. Any reference to an embodiment or component or action of the system and method herein referred to in the singular form may also include an embodiment including a plurality of such components, and any reference to any embodiment or component or action herein in the plural form may also include an embodiment including only a single component. References in the singular form or in the plural form are not intended to limit the currently disclosed system or method, and the embodiments, actions or components thereof. Terms such as "comprise", "include", "have", "contain", and "involve" and variations thereof used herein are intended to cover items listed thereafter and equivalents thereof and additional items. Reference to "or" may be considered inclusive so that any item using "or" may indicate any one of a single, more than one and all of the items described. Any reference to front and rear, left and right, top and bottom, upper and lower, and vertical and horizontal are intended to facilitate description instead of limiting the system and method or components thereof to any one position or spatial orientation.

Therefore, in a case that several aspects of at least one embodiment have been described, it should be understood that, various changes, modifications, and improvements are easily figured out by a person skilled in the art. Such changes, modifications, and improvements are intended to be part of the present invention and are intended to fall within the scope of the present invention. Therefore, the foregoing descriptions and drawings are merely exemplary, and the scope of the present invention should be determined from the correct construction of the appended claims and equivalents thereof.

The above-described embodiments of the present application are intended to be illustrative only. Numerous alternative embodiments may be devised by a person skilled in the art without departing from the scope of the following claims.

What is claimed is:
1. A therapeutic endoscope, comprising:
a main body including a protruding portion;
an image sensor unit accommodated in the protruding portion of the main body;
a connecting member having a first portion at least partially surrounding the protruding portion of the main body and a second portion extending from the first portion; and
a cover attached to the protruding portion of the main body by the connecting member, the cover including a first opening, a second opening opposite to the first opening, and a sidewall extending between the first opening and the second opening, wherein the sidewall of the cover includes a third opening connecting with the first opening and the second opening, wherein the second portion of the connecting member connects between the first portion of the connecting member and a boundary of the first opening of the cover, wherein a central axis of the first opening and a central axis of the second opening are aligned and pass through the image sensor unit, wherein the image sensor unit, the connecting member, and the cover are sequentially arranged along the central axis of the first opening, wherein a largest diameter of the connecting member is equal to a largest diameter of the cover, and wherein the connecting member has a sidewall defining a fourth opening connecting with the third opening of the sidewall of the cover, and wherein the fourth opening tapers from the third opening toward the image sensor unit and the third opening tapers from the fourth opening toward the second opening of the cover.

2. The therapeutic endoscope according to claim 1, wherein the central axis of the first opening and the central axis of the second opening are directed in a direction, and wherein the second portion of the connecting member connects between the first portion of the connecting member and the boundary of the first opening of the cover along the direction.

3. The therapeutic endoscope according to claim 2, wherein the second portion of the connecting member extends away from the central axis of the first opening in the direction.

4. The therapeutic endoscope according to claim 1, further comprising: a lens provided at a front end of the protruding portion of the main body, wherein the first portion of the connecting member at least partially surrounds the front end of the protruding portion of the main body.

5. The therapeutic endoscope according to claim 4, wherein the lens is exposed from the first portion of the connecting member and faces the first opening of the cover.

6. The therapeutic endoscope according to claim 1, wherein the protruding portion of the main body is free from passing through the cover.

7. The therapeutic endoscope according to claim 1, wherein the third opening extends fully along the sidewall of the cover from the first opening of the cover to the second opening of the cover, and wherein the third opening tapers from the second portion of the connecting member toward the second opening of the cover.

8. A therapeutic endoscope, comprising:
a main body including an image sensor unit;
a cover having a first opening, a second opening opposite to the first opening, and a sidewall extending between the first opening and the second opening, wherein the sidewall includes a third opening connecting with the first opening and the second opening; and
a connecting member configured to attach the cover to the main body,
wherein a central axis of the first opening and a central axis of the second opening are aligned and pass through the image sensor unit,
wherein the image sensor unit, the connecting member, and the cover are sequentially arranged along the central axis of the first opening,
wherein a largest diameter of the connecting member is equal to a largest diameter of the cover, and
wherein the connecting member has a sidewall defining a fourth opening connecting with the third opening of the sidewall of the cover, and wherein the fourth opening tapers from the third opening toward the image sensor unit and the third opening tapers from the fourth opening toward the second opening of the cover.

9. The therapeutic endoscope according to claim 8, further comprising:
a lens provided at a front end of a protruding portion of the main body, wherein the connecting member at least partially surrounds the front end of the protruding portion of the main body.

10. The therapeutic endoscope according to claim 9, wherein the lens faces the first opening of the cover.

11. The therapeutic endoscope according to claim 9, wherein the protruding portion of the main body is free from passing through the cover.

* * * * *